United States Patent [19]

Ackermann et al.

[11] 4,042,525
[45] Aug. 16, 1977

[54] IODOPHOR SOLUTION CONTAINING GLYCIDE POLYMER

[75] Inventors: Rolf Ackermann; Gerhard Morlock; Gerhard Stehlik, all of Hanau, Germany

[73] Assignee: Deutsche Gold- und Silber-Scheideanstalt vormals Roessler, Frankfurt am Main, Germany

[21] Appl. No.: 696,669

[22] Filed: June 16, 1976

[30] Foreign Application Priority Data

June 21, 1975 Germany .............................. 2527701

[51] Int. Cl.$^2$ .......................... C11D 3/48; C11D 7/26
[52] U.S. Cl. ................................ 252/106; 260/615 B; 260/615 P; 424/150; 424/78
[58] Field of Search ........ 252/106; 260/2 A, 30.4 EP, 260/615 B, 615 P; 424/78, 150

[56] References Cited

U.S. PATENT DOCUMENTS

| | | | |
|---|---|---|---|
| 2,977,278 | 3/1961 | Shelanski | 252/106 X |
| 3,067,089 | 12/1962 | Winslow | 424/78 |
| 3,150,096 | 9/1964 | Schmidt et al. | 252/106 |
| 3,519,559 | 7/1970 | Quinlan | 210/54 |
| 3,644,650 | 2/1972 | Sabatelli et al. | 424/341 |
| 3,650,966 | 3/1972 | Bakka | 252/106 |
| 3,984,341 | 10/1976 | Haschke et al. | 252/106 |
| 4,010,259 | 3/1977 | Johansson | 424/150 |

*Primary Examiner*—P.E. Willis, Jr.
*Attorney, Agent, or Firm*—Beveridge, DeGrandi, Kline & Lunsford

[57] ABSTRACT

An iodophor solution useful for disinfectant purposes comprising 0.5 to 4% by weight of iodine, 1.6 to 15% by weight of a water soluble glycide polymer, optionally 0 to 30% by weight of phosphoric acid, and water in an amount sufficient so that the solution comprises 100 weight percent.

26 Claims, No Drawings

IODOPHOR SOLUTION CONTAINING GLYCIDE POLYMER

BACKGROUND OF THE INVENTION

Field of the Invention

This invention relates to iodophor solutions comprising iodine, a water soluble glycide polymer, (i.e. polymer of glycidol, 2,3-epoxy-propanol-(1)) optionally phosphoric acid, and water in an amount sufficient so that the aqueous solution comprises 100 weight percent.

Iodophor solutions are aqueous solutions of complex iodine compounds with a content of active iodine of about 0.5 to about 4% by weight. The iodophor solution can be used as a disinfectant after dilution with water to the active iodine concentration required for any given application.

Iodophors and iodophor solutions are known in the art. Typical of these substances are iodophors and iodophor solutions based on polyvinyl pyrrolidone (U.S. Pat. No. 2,706,701). Such iodophors and iodophor solutions have the disadvantage that at most only 67% of their entire iodine content is available as active iodine for the purposes of disinfecting. According to the studies of Robert F. Cournoyer, Polymer Chemistry Edition 12, 603–612 (1964), this not only applies for iodine compounds, but also when elementary iodine alone is used in the production of polyvinyl pyrrolidone iodophors.

Iodophors based on surfactants are also known in the prior art (U.S. Pat. No. 2,977,315). In these iodophors the ratio of active iodine to total iodine is generally somewhat more favorable than in the case of polyvinyl pyrrolidone iodophors. However, the polyvinyl pyrrolidone iodophors have the disadvantage of being extremely viscous, and are therefore very difficult to pump. The polyvinyl pyrrolidone iodophors previously used in industrial systems required up to 65% of a relatively expensive viscosity lowering agent, e.g., hydroxy acetic acid (German Pat. No. 1,171,112) in order to make the products pumpable and thus industrially usable.

These surfactant-based iodophors exhibit a strong inclination to foaming rendering them unsuitable for many industrial purposes where the development of foam is undesirable. For example, they have not been found to be satisfactory with the newer methods of jet and heated high pressure jet spray cleaning employed in breweries.

Furthermore, iodophor solutions consisting of phosphoric acid, citric acid, sodium polymethacrylate, sodium xylene sulfonate, iodine, hydroiodic acid and water are known in the art (U.S. Pat. No. 3,150,096). These iodophor solutions exhibit the disadvantages of requiring precise amounts of various components. A further disadvantage of these solutions is that surface active compounds (sodium xylene sulfonate) have to be used for iodine solubilization, so that detergent-free iodophor solutions cannot be produced.

SUMMARY OF THE INVENTION

This invention provides an iodophor solution comprising a mixture of iodine, a water soluble glycide polymer, optionally phosphoric acid, and water in an amount sufficient so that the solution comprises 100% by weight. The solution can be more fully characterized in that it contains:

a. about 0.5 to about 4% by weight iodine,
b. about 1.6 to about 15% by weight of a glycide polymer, and
c. about 0 to about 30% by weight of phosphoric acid, wherein the quotient of the weight of glycide polymer to the weight of iodine is at least 3.33.

Iodophor solutions according to the invention can also have a relatively high concentration of iodine without the addition of ionic iodine compounds. The ratio of active to inactive iodine is, therefore, particularly favorable. The solutions are stable at high concentrations of phosphoric acid and when diluted exhibit non-foaming or only very slightly foaming disinfectant solutions.

The iodophor solutions can be used as disinfectants for the maintenance or re-establishment of hygienic operating conditions under a wide variety of applications from industry to agriculture, where non-hygienic conditions can influence or harm human health either directly, e.g., the operating conditions in hospitals, or indirectly, e.g., the infection of products of the food industry or agriculture. Therefore, it would be apparent to one skilled in the art that interest in these solutions would run the gamut from public health officials to large and small corporations and scientific technical associations.

Certain characteristics of iodophor solutions have been established by legal decisions, standards, norms and official rules. The composition of these iodophor solutions will vary depending upon the purpose for which they were intended and the place where they are used. For example, iodophor solutions for use as disinfectants for wounds, such as the well-known iodine tincture, will have characteristics differing from iodophor solutions for high-pressure jet cleaning of, for example, brewery kettles.

This invention provides an iodophor concentrate comprising the necessary substances, such as iodine, non-foaming solubilizers, and water, from which one can obtain iodophor solutions for various fields of application. The range of applications for the iodophor solutions can be expanded greatly through the addition of varying quantities of phosphoric acid and/or surface active substances.

PREFERRED EMBODIMENTS OF THE INVENTION

The iodophor solutions according to this invention contain a polymerization product of glycide as a water soluble polymer. The polymers can be homopolymers produced in a known manner by anionic or cationic polymerization of glycide, or copolymers containing up to 10 mole percent of other epoxides other than glycide. Examples of such other epoxides are: olefin oxides, such as ethylene oxide, propylene oxide, butylene oxide or styrene oxide; glycidol ethers, such as butyl glycidol ether or phenyl glycidol ether; and glycidol esters, such as glycidol acetate. A preferred copolymerization component is propylene oxide.

Particularly suitable homopolymers of glycide have a molecular weight between about 400 and about 2000 and an OH number between about 650 and about 800 mg KOH/g. Normally, these homopolymers have a water content of about 2.5 to about 4.0 percent by weight. The reduced viscosity of a 4% by weight solution in water at 20° C amounts to about 0.040 to about 0.080 dl/g.

Particularly suitable copolymers of glycide contain up to about 10 mole percent of another epoxide having a molecular weight between about 600 and about 1800, an OH number between about 550 and about 770 mg KOH/g and a water content of about 0.5 to about 3.0% by weight. The reduced viscosity of a 4% by weight copolymer solution in water at 20° C amounts to about 0.045 to about 0.070 dl/g.

In addition to the components already mentioned, the iodophor solutions can also contain organic solvents such as low molecular weight (e.g. $C_1$–$C_4$) alcohols, e.g., methanol, ethanol, n-propanol, isopropyl alcohol; low molecular weight carboxylic acids, e.g., acetic acid, propionic acid; ether alcohols, e.g., ethylene glycol monomethyl ether; glycols, e.g., ethylene glycol, 1,2- or 1,3-propylene glycol. N-propanol is a preferred solvent. Optionally, about 0.1 to about 4% by weight of water can be replaced in the finished iodophor solution by the above-mentioned organic solvents.

Optionally, ionic iodine compounds, such as hydrogen iodide, alkali metal iodides, alkaline earth metal iodides or ammonium iodide, along with the other solubilizers can be employed in the production of iodophor solutions of the present invention in order to accelerate the dissolution of iodine. Potassium iodide is a preferred iodide. The ionic iodine compounds can be employed in a quantity such that they comprise from about 0.1 to about 5% by weight of the finished iodophor solution.

Whenever a surface active agent can be tolerated in the iodophor solution of this invention, an anionic surfactant, such as sodium lauryl sulfate, sodium cumene sulfonate, or an alkyl benzene sulfonate, such as sodium dodecyl benzene sulfonate, can be added to the iodophor solution to increase the wetting power. The quantity of such wetting agents in the final composition of the iodophor solution is between about 0.5 to about 5% by weight.

The iodophor solutions according to the invention are produced by heating a mixture consisting of the polymerization product of glycide (homo- or copolymer) with water in a weight ratio of about 1 : 1 to about 4 : 1, preferably about 2 : 1 to about 3 : 1 with excess iodine for about 3 to about 5 hours while stirring at 90° to 100° C. Optionally, up to half the water can be replaced by n-propanol or another organic solvent and/or by an ionic iodine compound. This substitution increases the speed of the dissolution of the iodine and in the case of a slightly volatile solvent the sublimated iodine from the reaction vessel is washed back again from the reflux cooler into the reaction vessel. Upon completion of the reaction, the iodophor is diluted with water in a weight ratio of about 1 : 1, and then stirred for an additional 30 minutes at room temperature. The undissolved iodine is removed by either passing the solution through a glass frit or by centrifugation. Any desired iodine concentration can be achieved by dilution of the resulting clear solution with water. Phosphoric acid concentration of up to 30% by weight can be achieved independently of the iodine concentration by the addition of an 80 to 85% by weight phosphoric acid solution. Addition of the desired surface active substance takes place effectively after the addition of the phosphoric acid.

The iodophor solutions of this invention are customarily diluted to a weight ratio of 1 : 35 to 1 : 5000 with either distilled water, desalinated water or tap water. Surfactant-free iodophor solutions diluted with distilled water in a weight ratio of 1 : 500 to 1 : 2000 exhibit the same foaming behavior as pure water. Solutions with surfactants or without surfactants are stable and do not show any decrease in the active iodine content when stored at room temperature over a period of 6 months.

Following are examples illustrating and more fully explaining in detail this invention. All parts, proportions, percentages and ratios are by weight unless otherwise indicated.

EXAMPLE 1 a. Production of a Glycide Polymer

Within 10 minutes, 2.5 ml. of 25% aqueous sulfuric acid ($\Delta 7.5 \cdot 10^{-3}$ mole) are added drop by drop while stirring to 444 g of glycide (6 mole). At the same time, the temperature is kept at 70°–80° C during the dropwise addition and for approximately 30 minutes afterwards, cooling the reaction with ice when necessary. As soon as the temperature drops, it is stirred again for 1 hour with outside heating to 75° to 80° C. Subsequently, after the addition of 1 liter of water, it is neutralized with an anion exchanger in the OH form (for example Lewatite MP 62). The colorless solution is vacuum concentrated at 35° C and dried at 0.5 torr.

Yield: 450 g of very highly viscous oil
Water Content: 2.35% by weight
Viscosity: eta-red 0.059 dl/g (4% in water, 20° C)
OH Number: 730 mg KOH/g
Molecular Weight: 1000 b. Production of an Iodophor Solution 7.5 of water and 5 g of iodine are added to 15 g of the glycide polymer produced according to (a) and heated while stirring for 4 hours to about 100° C. Then 30 g of water is added and stirring is continued for another half hour at ambient temperature. Undissolved iodine is removed by passage through a glass frit. After addition of 56.6 g of 85% phosphoric acid and 47.8 g of water, the solution has the following composition (the iodine content is determined titrimetrically):

| | | |
|---|---|---|
| Polyglycide | 15.0 g | 9.4% by weight |
| Water | 93.8 g | 58.6% by weight |
| Iodine | 3.2 g | 2.0% by weight |
| Phosphoric acid (100%) | 48.0 g | 30.0% by weight |
| Total | 160.0 g | 100.0% by weight |

EXAMPLE 2 a. Production of a Glycide Polymer 0.4 ml of a $BF_3$ etherate (48% $BF_3$) diluted in the ratio of 1 : 20 with diethyl ether is added while cooling in an ice bath and while stirring in 370 g of glycide (5 mole), whereby the temperature within 1 hour rises to 80° C. Then 0.2 ml of $BF_3$ solution is added drop by drop and the temperature is kept between 80° and 90° C by heating. After cooling to ambient temperature, approximately 700 ml of water is added and the resultant mixture is neutralized with an anion exchanger in the OH form (for example, Lewatite MP 62). The colorless solution is condensed by means of vacuum at 35° C and dried at 0.5 torr.

| | |
|---|---|
| Yield: | 385 g of very highly viscous oil |
| Water Content: | 2.3% by weight |
| Viscosity: | eta-red 0.069 dl/g (4% in water, 20° C) |
| OH Number: | 650 mg KOH/g |
| Molecular Weight: | 1600 | b. Production of an Iodophor Solution 2.5 g of water, 2.5 g of n-propanol and 6 g of iodine are added to 15 g of the glycide polymer produced according to (a) and heated to 100° C while stirring for 3 hours. Then 20 g of water is added and stirring is continued for another half hour at ambient temperature. Non-dissolved iodine is removed by passage through a glass frit. After the addition of 34.4 g of 85% phosphoric acid and of 19.2 g of water, the solution has the following composition (the iodine content was determined titrimetrically):

| Polyglycide: | 15.0 g | 15.4% by weight |
|---|---|---|
| Water: | 46.9 g | 48.0% by weight |
| Iodine: | 3.9 g | 4.0% by weight |
| n-propanol: | 2.5 g | 2.6% by weight |
| Phosphoric acid (100%) | 29.2 g | 30.0% by weight |
| Total: | 97.5 g | 100.0% by weight |

EXAMPLE 3 a. Production of a Glycide Polymer 0.56 g of KOH (0.01 mole) and 6.2 g of ethylene glycol (0.1 mole) are put in a reaction vessel at 80° C and 74 g of glycide (1 mole) are added drop by drop under a nitrogen atmosphere within 2 hours. During this period, the reaction temperature rises to 90° C. Stirring of the reaction mixture is continued over night at ambient temperature. Subsequently, the reaction is diluted with 200 ml of water and neutralized with a cation exchanger in the H form (for example, Amberlite type Amberlyst 15). The solution is condensed in a vacuum at 35° C and dried at 0.5 torr.

| Yield: | 77 g viscous oil |
|---|---|
| Water Content: | 3.8% by weight |
| Viscosity: | eta-red 0.040 dl/g (4% in water, 20° C) |
| OH Number: | 780 mg KOH/g |
| Molecular Weight: | 550 . | b. Production of an Iodophor Solution 5 g of water and 5 g of iodine are added to 10 g of the glycide polymer produced according to (a) and heated to 100° C while stirring for 4 hours. Then 20 g of water are added and stirring is continued for another half hour at ambient temperature. Undissolved iodine is removed by passage through a glass frit. After the addition of 28.7 of 85% phosphoric acid and 31.85 g of water, the solution has the following composition (the iodine content was determined titrimetrically):

| Polyglycide | 10.0 g | 10.2% by weight |
|---|---|---|
| Water | 61.15 g | 62.8% by weight |
| Iodine | 1.95 g | 2.0% by weight |
| Phosporic acid (100%) | 24.4 g | 25.0% by weight |
| Total | 97.5 g | 100.0% by weight |

EXAMPLE 4 a. Production of a Copolymer 1 ml of 2.5% aqueous sulfuric acid is added to a mixture of 66.5 g of glycide (0.9 mole) and 5.8 g of propylene oxide (0.1 mole) drop by drop at room temperature while stirring within 15 minutes. During this period of addition, the temperature rises to 80° to 85° C. This temperature is maintained for 2.5 hours with the help of a water bath. After that, the solution is diluted with 150 ml of water and is neutralized with an anion exchanger in the OH form (Lewatite MP 62). The solution is condensed at 45° C and dried at 0.5 torr.

| Yield: | 73 g of highly viscous oil |
|---|---|
| Water Content: | 1.0% by weight |
| Viscosity: | eta-red = 0.055 dl/g (4% in water at 20° C) |
| Molecular Weight: | 810 |
| OH Number: | 630 mg KOH/g. | b. Production of an Iodophor Solution 7.5 g of water and 10 g of iodine are added to 15 g of the glycide copolymer produced according to (a) and heated to 100° C while stirring for 3 hours. Then 25 g of water are added and stirring is continued for another half hour at ambient temperature. Non-dissolved iodine is removed by passage through a glass frit. Next, 67.2 g of an 85% phosphoric acid and 71.5 g of water are added. The solution has the following composition (the iodine content was determined titrimetrically):

| Polyglycide | 15.0 g | 7.9% by weight |
|---|---|---|
| Water | 114.2 g | 60.1% by weight |
| Iodine | 3.8 g | 2.0% by weight |
| Phosphoric acid (100%) | 57.0 g | 30.0% by weight |
| Total | 190.0 g | 100.0% by weight |

EXAMPLE 5 An iodophor solution is produced according to Example 1; however, after the addition of the phosphoric acid, it is diluted with 44.6 g of water and reacted with 3.2 g of sodium lauryl sulfate. The solution has the following composition (the iodine content was determined titrimetrically):

| Polyglycide | 15.0 g | 9.4% by weight |
|---|---|---|
| Water | 90.6 g | 56.6% by weight |
| Iodine | 3.2 g | 2.0% by weight |
| Phosphoric acid (100%) | 48.0 g | 30.0% by weight |
| Surfactant (sodium laurylsulfate) | 3.2 g | 2.0% by weight |
| Total | 160.0 g | 100.0% by weight |

EXAMPLE 6

An iodophor solution is produced according to Example 2; however, after the addition of the phosphoric acid it is reacted with 17.2 g of water and 2.0 g of alkyl benzene sulfonate. The solution has the following composition (the iodine content was determined titrimetrically):

| Polyglycide | 15.0 g | 15.4% by weight |
|---|---|---|
| Water | 44.9 g | 46.0% by weight |
| Iodine | 3.9 g | 4.0% by weight |
| n-propanol | 2.5 g | 2.6% by weight |
| Phosphoric acid (100%) | 29.2 g | 30.0% by weight |
| Surfactant (alkyl benzene sulfonate) | 2.0 g | 2.0% by weight |
| Total | 97.5 g | 100.0% by weight |

What is claimed is:
1. An iodophor solution comprising:
 a. iodine in an amount of about 0.5 to about 4% by weight;
 b. a glycide polymer in an amount of about 1.6 to about 15% by weight;

c. phosphoric acid in an amount of about 0 to about 30% by weight;
d. water in an amount sufficient so that said solution comprises 100% by weight; and
wherein the quotient of the weight of said glycide polymer to the weight of said iodine is at least 3.33.

2. An iodophor solution according to claim 1, wherein the iodophor solution contains about 0.5 to about 5% by weight of surfactant selected from the group consisting of sodium lauryl sulfate, sodium cumene sulfonate, or sodium dodecyl benzene sulfonate.

3. An iodophor solution according to claim 1, wherein the solution is diluted with distilled water, desalinated water or tap water in a weight ratio of iodophor solution : dilutant of about 1 : 35 to about 1 : 5000.

4. An iodophor solution according to claim 1, wherein said iodophor solution contains about 0.1 to about 5% by weight of hydrogen iodide, an alkali metal iodide, an alkaline earth metal iodide, ammonium iodide, or mixtures thereof.

5. An iodophor solution according to claim 4, wherein said alkali metal iodide is potassium iodide.

6. An iodophor solution as in claim 1, wherein said iodophor solution contains about 0.1 to about 4% by weight of a low molecular weight monovalent alcohol, a glycol or a low molecular weight carboxylic acid or mixtures thereof.

7. An iodophor solution as in claim 6, wherein said low molecular weight carboxylic acid is acetic acid, propionic acid or mixtures thereof.

8. An iodophor solution as in claim 6, wherein said glycol is selected from the group consisting of ethylene glycol, 1,2-propylene glycol, 1,3-propylene glycol, or mixtures thereof.

9. An iodophor solution as in claim 6, wherein said low molecular weight alcohol is selected from the group consisting of methanol, ethanol, n-propanol, isopropyl alcohol or mixtures thereof.

10. An iodophor solution according to claim 6, wherein said low molecular weight monovalent alcohol is an ether alcohol.

11. An iodophor solution according to claim 10, wherein said ether alcohol is ethylene glycol monomethyl ether.

12. An iodophor solution according to claim 6, wherein said monovalent alcohol is n-propanol.

13. An iodophor solution as in claim 1, wherein said glycide polymer is a homopolymer having a molecular weight of about 400 to about 2000 and an OH number of about 650 to about 800 mg KOH/g.

14. An iodophor solution according to claim 13, wherein said homopolymer has a water content of about 2.5 to about 4.0 percent by weight and a reduced viscosity of a 4% by weight solution of said homopolymer in water at 20° C. of about 0.040 to about 0.080 dl/g.

15. An iodophor solution as in claim 1, wherein said glycide polymer is a copolymer comprising the product obtained from the polymerization of glycide and up to 10 mole percent of an other epoxide.

16. An iodophor solution as in claim 15, wherein said epoxide is selected from the group consisting of ethylene oxide, propylene oxide, butylene oxide or styrene oxide.

17. An iodophor solution as in claim 15, wherein said copolymer has a molecular weight of about 600 to about 1800 and an OH number of about 550 to about 770 mg KOH/g.

18. An iodophor solution according to claim 17, wherein said copolymer has a water content of about 0.5 to about 3.0% by weight and a reduced viscosity of a 4% by weight copolymer solution in water at 20° C. of about 0.045 to about 0.070 dl/g.

19. An iodophor solution as in claim 15, wherein said epoxide is a glycidol ester or a glycidol ether.

20. An iodophor solution as in claim 19, wherein said glycidol ether is selected from the group consisting of butyl glycidol ether and phenyl glycidol ether.

21. An iodophor solution as in claim 19, wherein said glycidol ester is glycidol acetate.

22. An iodophor solution according to claim 15, wherein said polymer is a copolymer of glycide and an olefin oxide.

23. An iodophor solution according to claim 15, wherein said epoxide is propylene oxide.

24. An iodophor solution according to claim 1, wherein said solution contains about 0.5 to about 5% by weight of an alkyl benzene sulfonate.

25. An iodophor solution according to claim 1, wherein said polymer is a homopolymer of glycide.

26. An iodophor solution according to claim 1, wherein said iodophor solution is surfactant-free and is diluted with distilled water in a weight ratio of 1 : 500 to 1 : 2000.

* * * * *